United States Patent
Malice, Jr. et al.

(10) Patent No.: US 6,443,986 B1
(45) Date of Patent: *Sep. 3, 2002

(54) SELF-FORMING PROSTHETIC DEVICE AND METHOD OF MAKING THE SAME

(75) Inventors: Louis F. Malice, Jr., Marietta; Robert James Halley, Decatur; Donna Mines, Ellenwood, all of GA (US)

(73) Assignee: Coloplast Corp, Marietta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/528,790

(22) Filed: Mar. 13, 2000

Related U.S. Application Data

(63) Continuation-in-part of application No. 09/267,319, filed on Mar. 12, 1999, now Pat. No. 6,162,250.
(60) Provisional application No. 60/077,728, filed on Mar. 12, 1998.

(51) Int. Cl.⁷ .................................................. A61F 2/52
(52) U.S. Cl. ................................ 623/7; 623/8; 264/222
(58) Field of Search ........................... 264/222; 450/38; 623/7, 8; 128/898

(56) References Cited

U.S. PATENT DOCUMENTS

| | | | | |
|---|---|---|---|---|
| 2,598,003 A | * | 5/1952 | Leo et al. ...................... | 450/38 |
| 4,024,876 A | * | 5/1977 | Penrock ........................ | 450/38 |
| 4,100,627 A | | 7/1978 | Brill, III .......................... | 3/36 |
| 4,317,241 A | | 3/1982 | Knoche .......................... | 3/36 |
| 4,401,492 A | | 8/1983 | Pfrommer ...................... | 156/61 |
| 4,787,905 A | | 11/1988 | Loi ................................. | 623/7 |
| 4,790,848 A | | 12/1988 | Cronin .......................... | 623/8 |
| 5,067,965 A | | 11/1991 | Ersek et al. ................... | 623/66 |
| 5,071,433 A | | 12/1991 | Naestoft et al. ............... | 623/7 |
| 5,258,036 A | * | 11/1993 | Edenbaum et al. .......... | 264/222 |
| 5,352,307 A | | 10/1994 | Wild ............................. | 156/66 |
| 5,407,445 A | | 4/1995 | Tautvydas et al. .............. | 623/8 |
| 5,411,554 A | | 5/1995 | Scopelianos et al. .......... | 623/8 |
| 5,534,609 A | * | 7/1996 | Lewis et al. .................... | 528/15 |
| 5,658,329 A | | 8/1997 | Purkait ........................ | 623/11 |
| 5,713,960 A | | 2/1998 | Christensen et al. .......... | 623/11 |
| 5,738,812 A | | 4/1998 | Wild ............................ | 264/102 |
| 5,741,877 A | | 4/1998 | Tiffany ........................ | 528/15 |
| 5,810,749 A | * | 9/1998 | Maas ............................. | 602/6 |
| 5,823,852 A | * | 10/1998 | Chu ............................. | 450/38 |
| 5,824,075 A | | 10/1998 | Thielbar ........................ | 623/7 |
| 5,888,231 A | * | 3/1999 | Sandvig et al. ................ | 623/36 |
| 5,902,335 A | * | 5/1999 | Snyder, Jr. ....................... | 623/7 |
| 5,941,909 A | | 8/1999 | Purkait ............................. | 3/36 |
| 6,113,635 A | * | 9/2000 | Gehl ............................. | 623/7 |
| 6,156,065 A | * | 12/2000 | Eaton ............................. | 623/7 |
| 6,162,250 A | * | 12/2000 | Malice, Jr. et al. ............. | 623/7 |
| 6,283,820 B1 | * | 9/2001 | Huang .......................... | 450/57 |

* cited by examiner

Primary Examiner—David H. Willse
Assistant Examiner—Suzette J. Jackson
(74) Attorney, Agent, or Firm—Needle & Rosenberg, P.C.

(57) ABSTRACT

The present invention is directed to a self-forming prosthetic device. The present invention is further directed to a method of making the self-forming prosthetic device. In addition, the present invention is directed to a new bra for use with a prosthetic device in the form of a breast prosthesis.

33 Claims, 1 Drawing Sheet

SELF-FORMING PROSTHETIC DEVICE AND METHOD OF MAKING THE SAME

RELATED APPLICATIONS

The present patent application is a continuation-in-part of U.S. Ser. No. 09/267,319, now U.S. Pat. No. 6,162,250 issued on Dec. 19, 2000, which patent claims the benefit of priority to U.S. Provisional Patent Application Ser. No. 60/077,728, filed on Mar. 12, 1998.

FIELD OF THE INVENTION

The present invention is directed to a self-forming prosthetic device. The present invention is further directed to a method of making the self-forming prosthetic device.

BACKGROUND OF THE INVENTION

Prosthetic devices are utilized in a variety of applications today. Breast prosthetics are a common type of prosthetic device. Other types of prosthetic devices include stump pads, shoe inserts, and the like. A variety of prosthetic devices have been developed to provide comfort to a patient. These prosthetic devices comprise specific materials and have a specific shape in order to provide a desired feel and comfort level to the patient. However, there continues to be a need for improved prosthetic devices, including stump pads and shoe inserts, which have a desired shape, feel and comfort for patients.

In the event of breast cancer, surgeons often perform mastectomies in order to remove all or part of the cancerous breast. In recent years, surgeons have increasingly utilized partial mastectomies, such as lumpectomies and quadrectomies, when they are sufficient to remove the cancerous tissue from the breast.

In cases involving complete mastectomies, patients can choose from a wide variety of prosthetic devices in order to provide a symmetrical appearance under clothing. Patients who undergo partial mastectomies are presently able to choose a partial prosthesis. Presently, partial breast prostheses are offered in a few different shapes, with each shape being available in a few different sizes. The patient must select an off-the-shelf partial prosthesis having a shape and size that provides the patient with the most symmetry under clothing.

In many cases, the off-the-shelf partial prosthesis have shapes and sizes, which do not provide a good fit with the remaining portion of the patient's breast. Moreover, occasionally, because of scars or tissue wounds, even patients with full mastectomies can not find prostheses that provide a good fit. Therefore, there exists a need in the art for a prosthetic device that can be custom tailored to the size and shape of the patient's breast.

In other prosthetic applications, patients have similar difficulties finding an off-the-shelf prosthetic device having the desired shape and size to provide a good fit with the remaining portion of the patient's body. Because of these and other difficulties associated with current prosthetic devices, there exists a need in the art for a prosthetic device that can be custom tailored to the size and shape of the patient's body.

SUMMARY OF THE INVENTION

The present invention provides a self-forming prosthetic device, which conforms to a portion of a patient's body, such as a chest wall, a partial breast, a partial leg, a partial foot, or any other part of the body. The prosthetic device is formed from a prosthetic device precursor, which includes at least two separate compartments A and B, wherein compartment A contains a curable material and compartment B contains at least one of a catalyst and a cross-linking agent. In one embodiment, the prosthetic device precursor is formed such that one of compartments A and B comprises a bag, and the other of compartments A and B comprises a capsule within the bag. In a further embodiment, the prosthetic device precursor is formed such that compartments A and B are separate chambers within a bag, separated from one another by an interior film. When the prosthetic device precursor is ready to be fitted, the catalyst or cross-linking agent is mixed with the curable material. The prosthetic device precursor is then placed next to a patient's body, such as in the patient's bra, and cures to form a prosthetic device in the shape of the "mold" formed by the patient's chest wall or breast, and bra.

The present invention is further directed to a method of making a prosthetic device precursor and a self-forming prosthetic device. The method of manufacture enables the production of a prosthetic device, which conforms specifically to a given patient's body or any other desired shape.

The present invention is also directed to a variety of uses for the self-forming prosthetic device. The various aspects of the present invention may be more clearly understood and appreciated from a review of the following detailed description of the disclosed embodiments.

DETAILED DESCRIPTION OF THE INVENTION

Figure 1:
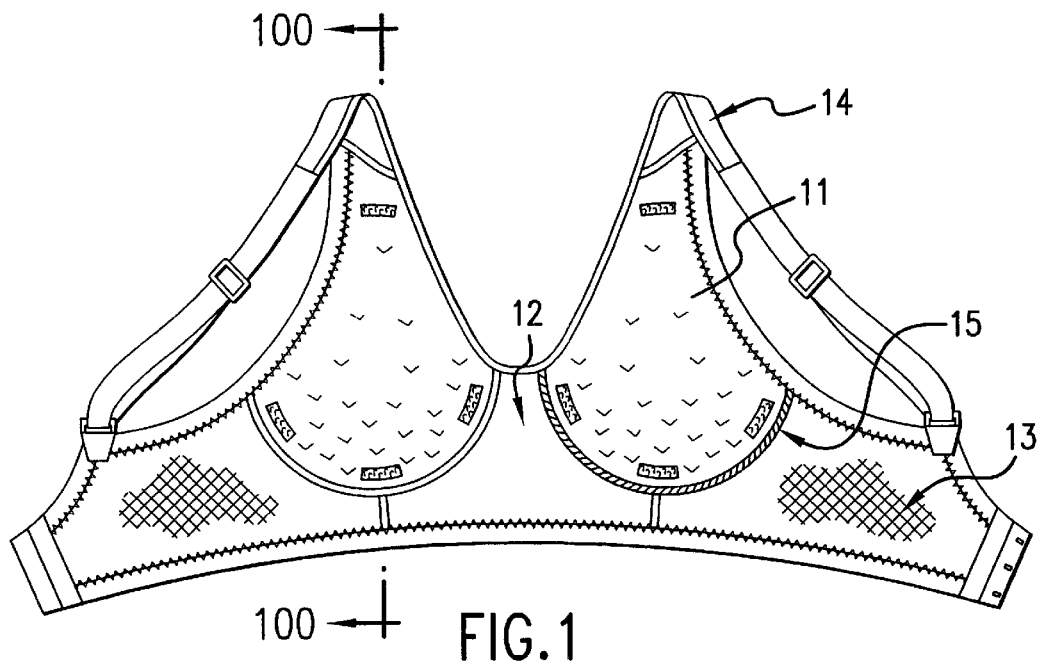
FIG. 1 depicts a rear view of a bra of the present invention.

The present invention provides a self-forming article of manufacture, which is simple to use and quickly conforms to its surroundings. The present invention is further directed to a method of making a self-forming article of manufacture and the multiple uses for the resulting article. The self-forming article of manufacture may be used in any application that requires a molded object having a desired degree of softness and conformability. Suitable uses include, but are not limited to, using the self-forming article of manufacture as a prosthetic device, stump pad, shoe insert, or other molded object. A particular suitable application for the self-forming article of manufacture is in the area of breast prosthesis. As disclosed throughout the specification, the self-forming article of manufacture is referred to as a self-forming prosthetic device made from a prosthetic device precursor. However, it should be noted that the self-forming article of manufacture has many uses other than as a prosthetic device.

In one embodiment of the present invention, the self-forming article of manufacture is a prosthetic device that conforms to a patient's body (hereinafter referred to as "a self-forming prosthetic device"). The self-forming prosthetic device is suitable for use with any portion of a patient's body, including, but not limited to, the patient's chest wall, breast, leg, and foot. The self-forming prosthetic device of the present invention allows a patient to choose an uncured, conformable prosthetic device precursor, which may be easily transformed into a cured, prosthetic device having a shape, which conforms to the patient's body and provides comfort and satisfaction to the patient.

The self-forming prosthetic device of the present invention is formed from a prosthetic device precursor. The prosthetic device precursor comprising at least two separate compartments A and B, wherein compartment A contains a curable material and compartment B contains at least one of a catalyst and a cross-linking agent. In one embodiment of the present invention, the prosthetic device precursor comprises compartments A and B, wherein one of compartments A and B comprises a bag, and the other of compartments A and B comprises a capsule within the bag. In this embodiment, a bag is filled with a curable material, a capsule within the bag, and one or more materials within the capsule. The one or more materials within the capsule may include materials such as catalysts, cross-linking agents, and pigments as described below. The bag may be formed from a thin film material having a desired appearance and texture. The bag may comprise a variety of materials including, but not limited to, thermoplastic film-forming materials such as polyurethane, polyethylene, polypropylene, and polyester. Other suitable materials include castable or curable film-forming materials such as polyurethanes, silicones, and castable rubbers. Desirably, the bag material comprises one or more layers of a thin polyurethane film. The edges of the bag are sealed to form a shape having a desired volume. The film material used to form the bag desirably has a film thickness of up to about 5 mil. In one embodiment of the present invention, the film material has a film thickness of from about 1 mil to about 3 mil.

Although the bag may be made as described above, it should be noted that the bag may be made by any other method known to those of ordinary skill in the art. Suitable alternative methods for forming the bag include, but are not limited to, blow molding, dip coating of male molds, and spray coating of female molds. Further, it should be noted that the film of the bag may be modified as desired prior to or after bag formation. The appearance and texture of the film may also be modified after the bag is filled with curable material as described below. Suitable film treatments include, but are not limited to, thermoforming, laminating, embossing, texturing, pigmenting, or any other process, which gives the film a more realistic, comfortable, or attractive appearance and feel.

In one embodiment, the film is thermoformed into a desired three-dimensional shape prior to forming the bag. In the case of a breast prosthesis, the film may be thermoformed, pigmented, and/or laminated to form a nipple for the final breast prosthesis. In one embodiment, a film embossed with a skin-like texture is used to make the bag. In another embodiment, a non-woven polyurethane material is laminated to the outside of the bag to create a more pleasing texture. Other modifications to the bag include, but are not limited to, the incorporation of a valve into the bag. The valve enables the injection or removal of curable material from the bag to adjust the volume of the prosthetic device precursor. In addition, the valve may be used to inject one or more other materials into the bag, such as a catalyst or cross-linking agent to initiate or adjust the cure of the curable material within the bag. Any valve may be used in the present invention as long as the valve is attachable to the bag and functions as desired. Desirably, the valve comprises a septum device, a ball cone check valve, or simply a tube extension of the bag that is heat sealed after injection of the curable material.

The bag is filled with an uncured material, which may be cured to form a hardened material having a desired amount of softness and texture. Suitable curable materials include, but are not limited to, silicone gels and silicone gel systems, which cure at room temperature with the aid of at least one catalyst or cross-linking agent. The choice of a particular curable material may be made by one of ordinary skill in the art given a patient's particular needs (i.e., degree of softness, etc.). Suitable curable materials are well known in the art of making prosthetic devices, and any one may be used in the present invention. Suitable curable materials are disclosed in numerous publications including, but not limited to, U.S. Pat. Nos. 5,534,609 and 5,741,877, both of which are incorporated by reference.

In one embodiment of the present invention, the curable material comprises a polydimethylsiloxane (CAS Reg. No. 63148-62-9), a vinyldimethylsiloxy terminated polydimethylsiloxane (CAS Reg. No. 68951-99-5), a methylhydrosiloxane-dimethylsiloxane copolymer (CAS Reg. No. 68037-59-2), a hydride terminated polydimethylsiloxane, or a combination thereof. In addition to the curable material, other materials may be combined with the curable material. Other additives include, but are not limited to, silicone oil, colorants, viscosity modifiers, cure inhibitors, cure accelerators, and fillers. Once the bag is filled with the curable material and optional additives, one or more capsules may be inserted into the bag. It should be noted that the order of insertion of materials into the bag is not important. In other words, one or more capsules may be placed in the bag prior to or after the curable material.

The capsule may be formed from any material, which provides a temporary enclosure for one or more encapsulated materials. Suitable materials for forming the capsule include, but are not limited to, polyethylene film, vinylidene chloride-containing copolymers, polyvinylidene chloride film, polyester film, polyvinyl chloride film, and polyurethane film. Desirably, the capsule is formed from a polyethylene film, available from Larsen Packaging (Fairmont, Minn.) or a SARAN™ film, available from Dow Chemical (Midland, Mich.).

In one embodiment of the present invention, a capsule is formed from polyethylene film by forming an envelope from one or more sheets of polyethylene film and heat sealing the edges of the film with pressure. It should be noted that the edges of the capsule may be sealed by any other method known to those of ordinary skill in the art. Suitable methods for sealing the edges of the capsule include, but are not limited to, adhesively sealing the edges of the capsule.

The capsule may be a component separate from the above-described bag, or may be an integral part of the bag. In the case where the capsule is an integral part of the bag, the capsule may be represented as one chamber of a multi-chamber bag. In this embodiment, the prosthetic device precursor comprises a multi-chamber bag, having compartments A and B, which are separated from one another by an interior film. The curing material may be injected into its chamber (compartment A or B) through a first fill port. The catalyst or cross-linking agent may be injected into its chamber (compartment B or A) through a second fill port. Once the fill ports are sealed, the self-forming precursor may be squeezed to break the film separating the two chambers. It should be noted that at least a portion of the film separating the two chambers may be made weaker (i.e., have a lower burst strength) than the outer film material of the bag. For example, the thickness of the film separating the two chambers may (1) have a thickness less than the remaining film of the bag and/or (2) be formed from a different material, having a lower burst strength than the film material of the bag. Alternatively, a removable plug or a valve may be present in the wall of the film separating the two chambers. In any case, once the film separating the two chambers is broken, the prosthetic device precursor material is kneaded, and cures into a desired shape.

One or more encapsulated materials may be present in one or more compartments of the prosthetic device precursor. In one embodiment of the present invention, a catalyst material is enclosed within the capsule or placed within a chamber of the bag. The catalyst material may be any catalyst material, which initiates the curing process of the curable material. Suitable catalyst materials include, but are not limited to, platinum-containing catalysts. Suitable platinum-containing catalysts are disclosed in numerous publications including, but not limited to, U.S. Pat. Nos. 5,534,609 and 5,741,877, both of which are incorporated by reference. Desirably, the catalyst material comprises a platinum-silicone complex. As used herein, the term "platinum-silicone complex" is used to describe a silicone-complexed-platinum species dissolved in silicone oil. Such catalysts are available from a number of sources including, but not limited to, Catalyst PTS C OL (Wacker-Chemie GmbH; Germany), and Catalyst PC085 (United Chemical Technologies). The amount of catalyst may vary depending upon the desired rate of cure and the curable material. Desirably, the amount of catalyst is up to about 3 wt % based on the total weight of catalyst and curable material. In one embodiment of the present invention, the amount of catalyst is from about 0.5 wt % to about 1.0 wt % based on the total weight of catalyst and curable material. In addition to the catalyst material, one or more additional materials may be combined and encapsulated along with the catalyst. Suitable additional materials include, but are not limited to, the above-mentioned additives. Once the curable material, capsule, and other additives are positioned within the bag, the fill port of the bag may be sealed.

In another embodiment of the present invention, a cross-linking agent is enclosed within the capsule or placed within a chamber of the bag. In this embodiment, the catalyst may be in the capsule or chamber along with the cross-linking agent or may be incorporated into the curable material within the sealed bag. The cross-linking agent may be any cross-linking agent, which enables cross-linking of the curable material within the bag. Suitable cross-linking materials include, but are not limited to, hydride terminated polysiloxanes and hydride-containing polysiloxanes. Suitable cross-linking materials are disclosed in numerous publications including, but not limited to, U.S. Pat. Nos. 5,534,609 and 5,741,877, both of which are incorporated by reference. Desirably, the cross-linking material comprises hydride terminated polysiloxanes or hydride-containing polysiloxanes available from United Chemical Technologies, Bristol, Pa. Although the hydride content of the cross-linking material may vary depending on a number of factors including the degree of cross-linking desired, cross-linking materials having a hydride content of from about 0.5 to about 10.0 mmol/g of cross-linking material are particularly suitable for the present invention. The amount of cross-linking material may vary depending upon the desired rate of cross-linking and the curable material. Desirably, the amount of cross-linking material is up to about 10 wt % based on the total weight of the curable composition, which includes any catalyst, cross-linking material, curable material, and additives. In one embodiment of the present invention, the amount of cross-linking material is from about 0.5 wt % to about 1.5 wt % based on the total weight of the curable composition.

In a further embodiment of the present invention, a prosthetic device precursor and a self-forming prosthetic device are formed from an outer bag of polyurethane and a curable silicone mixture comprising one or more polydimethylsiloxanes (CAS Reg. No. 63148-62-9) and one or more silicone vinyl polymers or vinyldimethylsiloxy terminated polydimethylsiloxanes (CAS Reg. No. 68951-99-5) in combination with one or more silicone hydride polymers or methylhydrosiloxane-dimethylsiloxane copolymers (CAS Reg. No. 68037-59-2). Desirably, the polydimethylsiloxane has a viscosity of from about 100 cSt to about 10,000 cSt. More desirably, the polydimethylsiloxane has a viscosity of from about 100 cSt to about 1,000 cSt. Desirably, the vinyldimethylsiloxy terminated polydimethylsiloxane has a viscosity of from about 1,000 cSt to about 165,000 cSt, and the methylhydrosiloxane-dimethylsiloxane copolymer has a viscosity of from about 5 cSt to about 1,000 cSt and a hydride content of from about 0.5 to about 5.0 mmol/g.

The present invention is further directed to a process of forming an article of manufacture. The process may be used to form a variety of custom molded articles having a desired size, color, and softness, while providing substantially complete conformity to a desired surface, such as a patient's body. In one embodiment of the present invention, a precursor to the article of manufacture is produced as described above, wherein the precursor comprises at least two separate compartments A and B, wherein compartment A contains a curable material and compartment B contains at least one of a catalyst and a cross-linking agent. As discussed above, the prosthetic device precursor may comprise a bag (compartment A) and a capsule (compartment B) within the bag, or the prosthetic device precursor may comprise a multi-chamber bag, wherein compartments A and B are separate chambers within the bag, separated from one another by an interior film. The capsule or interior film within the bag is broken so that the contents of compartments A and B may be intermixed. Desirably, the resulting mixture is mixed for about 5 to 10 minutes by kneading the precursor. The precursor is then placed in a mold or other three-dimensional space, such as within a bra next to a patient's body in the case of a breast prosthesis. The precursor is allowed to cure for about 15 minutes. The resulting prosthesis conforms to the mold or three-dimensional space, such as a patient's existing body profile.

In a further embodiment of the present invention, a variety of attachment systems, such as hook-and-loop fasteners, are easily adhered to the bag material to provide a durable and reliable means of attaching the prosthetic device to either the patient's body or to a patient's garment if desired. Suitable attachment systems include, but are not limited to, those disclosed in U.S. Pat. No. 5,071,433 to Naestoft et al. and U.S. Pat. No. 5,352,307 to Wild, both of which are incorporated by reference in their entirety.

The prosthetic device of the present invention may be prepared in a variety of ways. In one desired embodiment, two layers of polyurethane film are heat sealed together to form an oval bag with an inlet port on one end of the oval bag. A small capsule containing a platinum catalyst in silicone oil is placed into the bag through the inlet port. A mixture of silicone curable materials is injected into the bag. The mixture is formulated to cure at room temperature when mixed with the platinum catalyst. Entrapped air is removed from the bag, and the inlet is heat sealed. A patient is fitted with the prosthetic device precursor, which has the proper size and shape to match the patient's needs. The capsule of catalyst is broken open and the bag is kneaded for approximately 5–10 minutes in order to thoroughly mix the catalyst into the curable silicone mixture. The bag is then placed in a desired three-dimensional space, such as in a patient's bra in the position in which the prosthetic device will be worn.

After approximately 15 minutes, the liquid cures into a silicone gel, which conforms to the desired three-dimensional space. It should be noted that mix time and cure time may vary depending on the curable material used, the catalyst, the size of the prosthetic device, and other factors.

Alternatively, the prosthetic device of the present invention may be prepared as follows. Two layers of polyurethane film are heat sealed together to form an oval bag with an inlet port on one end of the oval bag. A small capsule containing a cross-linking material is placed into the bag through the inlet port. A mixture of curable materials and catalyst is injected into the bag. The mixture is formulated to cross-link at room temperature when mixed with the cross-linking material. Entrapped air is removed from the bag, and the inlet is heat sealed. A patient is fitted with the prosthetic device precursor, which has the proper size and shape to match the patient's needs. The capsule of cross-linking material is broken open and the bag is kneaded for approximately 5–10 minutes in order to thoroughly mix the cross-linking material into the curable silicone mixture. The bag is then placed in a desired three-dimensional space, such as within a patient's shoe in the position in which the prosthetic device will be worn. After approximately 15 minutes, the liquid cures into a silicone gel, which conforms to the desired three-dimensional space. As discussed above, mix time and cure time may vary depending on the curable material used, the cross-linking material, the size of the prosthetic device, and other factors.

In a further embodiment of the present invention, a multi-layer prosthetic device may be formed, wherein at least one layer of the multi-layer prosthetic device comprises the self-forming prosthetic device of the present invention. One example of such a multi-layer prosthetic device is a two-layer prosthetic device, wherein the front or outermost layer of the prosthetic device comprises a first pre-cured prosthetic device and the back or body-side layer comprises the self-forming prosthetic device of the present invention. The pre-cured prosthetic device layer may provide a pre-formed shape or other attribute to the resulting prosthetic device, while the self-forming layer provides a desired feel and comfort level for a patient. A two-layer prosthetic device may be used as a breast prosthesis, wherein the pre-cured prosthetic device layer comprises breast components such as a nipple, while the self-forming portion provides conformability and comfort to the wearer's chest.

In one embodiment of the present invention, the self-forming prosthetic device may be used as a partial or full breast prosthesis. The self-forming prosthetic device conforms to a specific wearer's chest wall and/or partial breast, a portion of which having been removed during a partial mastectomy procedure. In this embodiment, the self-forming breast prosthesis may be used with any commercially available bra. In addition, the self-forming breast prosthesis may be used with a new bra as described below and shown in FIGS. 1 and 2.

The new bra may be a soft-cup and/or underwire bra with a molded foam inner cup and means for attaching a prosthetic device, such as the above-described self-forming breast prosthesis, to an inner surface of the cup. Suitable attachment means may include, but are not limited to, hook-and-loop fasteners, adhesives, and snaps. Desirably, the attachment means comprises a loop lining on an inner surface of the cup and a hook material on the prosthetic device. Suitable loop linings include, but are not limited to, Perma Loop and Brushed Tricot, both of which are 100% polyester fabrics available from Gehring Textiles (New York, N.Y.).

Figure 2:
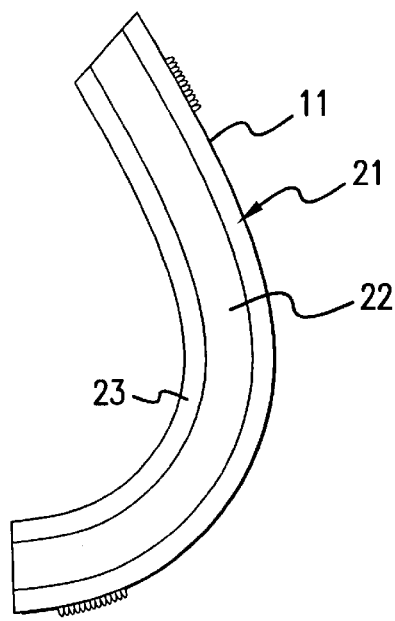
FIG. 2 depicts a vertical cross-section of a molded outer cup of a bra of the present invention along line 100 of FIG. 1.

In one embodiment of the present invention as shown in FIG. 1, the new bra may comprise one or more of the following main components: a molded cup 11; a center band 12; a back power net 13; and a strap extension 14 for a cushion shoulder strap. The molded cup 11 of the new bra is desirably a three ply material as shown in FIG. 2. The three ply material of molded cup 11 may comprise an outer cup layer 21, a middle cup layer 22, and an inner cup layer 23. The outer cup layer 21 may comprise any moldable fabric, which can be used in the production of bras. Suitable moldable fabrics include, but are not limited to, 100% polyester fabric sold as Simplex No. KTS516, available from McMurray Fabrics (Aberdeen, N.C.). The middle cup layer 22 may comprise any moldable foam material, which can be used in the production of bras. Suitable moldable foam materials include, but are not limited to, 100% polyurethane foam materials available from Moldworks, Inc. (Linden, N.J.). The inner cup layer 23 may comprise any attachment means described above. Desirably, the inner cup layer 23 comprises a loop material, and the loop material is laminated to a middle cup layer 23 in the form of a foam material.

The plies of the molded cup are desirably "over-edged" and then attached, by sewing, to strap extension 14. A center band 12 and back power net 13 may be attached to the molded cup with "bias binding" 15 for a smooth and comfortable finish. The new bra provides a mean for attaching a prosthetic device to the bra, as well as, provides support during the shaping process in the self-forming embodiment described above. The new bra provides a more symmetrical appearance when worn with a prosthetic device, than obtained from the prosthetic device alone.

The present invention is further described by the examples which follow. Such examples, however, are not to be construed as limiting in any way either the spirit or the scope of the present invention. In the examples, all chemical components are given in parts by weight, unless stated otherwise.

EXAMPLE 1

Formation of a Self-Forming Prosthetic Device Using a Capsule Containing a Catalyst Mixture A self-forming prosthetic device was formed using the following procedure. A bag was formed by heat sealing two sheets of polyurethane film having a thickness of 2.5 mil. at a temperature of about 385° F. and a pressure of about 25 bar for about 2 seconds.

A curable material was formed by mixing the following components:

Polydimethylsiloxane having a viscosity of 100 cSt . . . 350 g

Vinyldimethylsiloxy terminated polydimethylsiloxane having a viscosity of 2,000 cSt . . . 105 g Vinyldimethylsiloxy terminated polydimethylsiloxane having a viscosity of 65,000 cSt . . . 45 g Methylhydrosiloxane-dimethylsiloxane copolymer having a viscosity of 45 cSt, hydride content of 1.7 mmol/g . . . 4 g The curable composition was mixed and degassed.

A catalyst mixture was formed using the following components:

Platinum catalyst (platinum complexed to divinyltetramethylsiloxane dissolved in polydimethyl-siloxane, platinum content=2 wt %) . . . 1 g Polydimethylsiloxane having a viscosity of 100 cSt . . . 49 g The catalyst mixture was sealed in a small capsule having dimensions of about ¼" diameter and 1" length. The capsule was formed by folding a low molecular weight polyethylene film, PARAFILM™ (available from Van Waters & Rogers), into an envelope and heat sealing the edges of the envelope under pressure.

The capsule and about 125 g of the curable composition were inserted into the bag through a fill port. The fill port was heat sealed to form a prosthetic device precursor. The precursor was squeezed to break the capsule. The contents of the precursor were kneaded for about 5 to 10 minutes. The precursor was placed in a cradle and allowed to cure for about 15 minutes. The self-forming prosthetic device conformed to the shape of the cradle.

EXAMPLE 2

Formation of a Self-Forming Prosthetic Device Using a Capsule Containing a Cross-linking Mixture A self-forming prosthetic device was formed using the following procedure. A bag was formed by heat sealing two sheets of polyurethane film having a thickness of 2.5 mil. at a temperature of about 385° F. and a pressure of about 25 bar for about 2 seconds.

A curable material was formed by mixing the following components:

Polydimethylsiloxane having a viscosity of 100 cSt . . . 225.0 g
Vinyldimethylsiloxy terminated polydimethylsiloxane having a viscosity of 2,000 cSt . . . 60.0 g
Vinyldimethylsiloxy terminated polydimethylsiloxane having a viscosity of 65,000 cSt . . . 15.0 g
Platinum catalyst (platinum complexed to divinyltetramethylsiloxane dissolved in polydimethyl-siloxane, platinum content=2 wt %) . . . 0.11 g The curable composition was mixed and degassed.

A cross-linker mixture was formed using the following components:

Methylhydrosiloxane-dimethylsiloxane copolymer having a viscosity of 45 cSt, hydride content of 1.7 mmol/g . . . 29.2 g
Polydimethylsiloxane, hydride terminated having a viscosity of 15 cSt . . . 10.0 g A small capsule having dimensions of about ¼ inch diameter and 1 to 1.5 inch length was prepared using two sheets of Saran film (available from Dow Chemicals). The capsule was formed by heat sealing three sides of the sheets using an impulse sealer from American International Electric. About 1.4 g of the cross-linker mixture was placed in the capsule. Air was removed from the capsule and the fourth side was heat sealed.

The bag was placed in a mold. The capsule and about 150 g of the curable composition were inserted into the bag through a fill port. The mold was heated at approximately 120° C. for about 30 minutes to thermally form the precursor bag into a desired shape and to seal the fill port. After cooling, the bag was removed from the mold and trimmed to make the self-forming prosthetic device precursor.

The capsule inside the precursor was squeezed to burst the capsule. The contents of the capsule were then forced into the curable composition (i.e., similar to emptying a tube of toothpaste). The precursor was kneaded for about 5 to 10 minutes and then placed in a cradle. The precursor was allowed to cure for about 15 minutes. The self-forming prosthetic device conformed to the shape of the cradle.

EXAMPLE 3

Formation of a Self-Forming Prosthetic Device Having an Embossed Surface

A self-forming prosthetic device was formed using the following procedure. A bag was formed by heat sealing two sheets at a temperature of about 385° F. and a pressure of about 25 bar for about 2 seconds. One sheet of film was a polyurethane film having a thickness of 2.5 mil. The other sheet of film was a polyurethane film having a thickness of 2.5 mil and embossed with a skin-like texture.

A curable material was formed by mixing the following components:

Polydimethylsiloxane having a viscosity of 100 cSt . . . 750 g
Vinyldimethylsiloxy terminated polydimethylsiloxane having a viscosity of 2,000 cSt . . . 200 g
Vinyldimethylsiloxy terminated polydimethylsiloxane having a viscosity of 65,000 cSt . . . 50 g
Methylhydrosiloxane-dimethylsiloxane copolymer having a viscosity of 45 cSt, hydride content of 1.7 mmol/g . . . 6.77 g
Polydimethylsiloxane, hydride terminated having a viscosity of 15 cSt . . . 2.32 g The curable composition was mixed and degassed.

A catalyst mixture was formed using the following components:

Platinum catalyst (platinum complexed to divinyltetramethylsiloxane dissolved in polydimethyl-siloxane, platinum content=2 wt %) . . . 5.0 g
Polydimethylsiloxane having a viscosity of 100 cSt . . . 45.0 g A small capsule having dimensions of about ¼ inch diameter and 1 to 1.5 inch length was prepared using two sheets of Saran film (available from Dow Chemicals). The capsule was formed by heat sealing three sides of the sheets using an impulse sealer from American International Electric. About 0.35 g of the catalyst mixture was placed in the capsule. Air was removed from the capsule and the fourth side was heat sealed.

The capsule and about 100 g of the curable composition were inserted into the bag through a fill port. The fill port was then sealed using the impulse sealer from American International Electric. The bag was trimmed to make the self-forming prosthetic device precursor.

The capsule inside the precursor was squeezed to burst the capsule. The contents of the capsule were then forced into the curable composition (i.e., similar to emptying a tube of toothpaste). The precursor was kneaded for about 5 to 10 minutes and then placed in a cradle. The precursor was allowed to cure for about 15 minutes. The self-forming prosthetic device conformed to the shape of the cradle.

EXAMPLE 4

Formation of a Self-Forming Prosthetic Device Having an Textured Film Surface

A self-forming prosthetic device was formed using the following procedure. A bag was formed by heat sealing three sheets at a temperature of about 385° F. and a pressure of about 25 bar for about 2 seconds. Two sheets of film were polyurethane film having a thickness of 2.5 mil. The third sheet of film, used as an outer layer, was a non-woven polyurethane material (9905 WB elastic non-woven) available from 3M, St. Paul, Minn.

A curable material was formed by mixing the following components:

Polydimethylsiloxane having a viscosity of 100 cSt . . . 750 g

Vinyldimethylsiloxy terminated polydimethylsiloxane having a viscosity of 2,000 cSt . . . 200 g Vinyldimethylsiloxy terminated polydimethylsiloxane having a viscosity of 65,000 cSt . . . 50 g Methylhydrosiloxane-dimethylsiloxane copolymer having a viscosity of 45 cSt, hydride content of 1.7 mmol/g . . . 6.77 g Polydimethylsiloxane, hydride terminated having a viscosity of 15 cSt . . . 2.32 g The curable composition was mixed and degassed.

A catalyst mixture was formed using the following components:

Platinum catalyst (platinum complexed to divinyltetramethylsiloxane dissolved in polydimethyl-siloxane, platinum content=2 wt %) . . . 5.0 g Polydimethylsiloxane having a viscosity of 100 cSt . . . 45.0 g A small capsule having dimensions of about ¼ inch diameter and 1 to 1.5 inch length was prepared using two sheets of Saran film (available from Dow Chemicals). The capsule was formed by heat sealing three sides of the sheets using an impulse sealer from American International Electric. About 0.45 g of the catalyst mixture was placed in the capsule. Air was removed from the capsule and the fourth side was heat sealed.

About 125 g of the curable composition were inserted into the bag between the two layers of polyurethane film through a fill port. The precursor was positioned in a mold so that the fill port would not be sealed and the curable composition would not leak out. The mold was heated at approximately 250° C. for about 30 minutes to thermally form the precursor bag into a desired shape and to heat seal the non-woven layer to the adjacent polyurethane layer. The capsule was then placed in the precursor bag through the fill port. The fill port was then sealed using the impulse sealer from American International Electric. The bag was trimmed to make the self-forming prosthetic device precursor.

The capsule inside the precursor was squeezed to burst the capsule. The contents of the capsule were then forced into the curable composition (i.e., similar to emptying a tube of toothpaste). The precursor was kneaded for about 5 to 10 minutes and then placed in a cradle. The precursor was allowed to cure for about 15 minutes. The self-forming prosthetic device conformed to the shape of the cradle.

EXAMPLE 5

Formation of a Self-Forming Prosthetic Device Using a Capsule Containing a Cross-linking Mixture and a Pigment A self-forming prosthetic device was formed using the following procedure. A bag was formed by heat sealing two sheets of polyurethane film having a thickness of 2.5 mil. at a temperature of about 385° F. and a pressure of about 25 bar for about 2 seconds.

A curable material was formed by mixing the following components:

Polydimethylsiloxane having a viscosity of 100 cSt . . . 750.0 g

Vinyldimethylsiloxy terminated polydimethylsiloxane having a viscosity of 2,000 cSt . . . 200.0 g Vinyldimethylsiloxy terminated polydimethylsiloxane having a viscosity of 65,000 cSt . . . 50.0 g Platinum catalyst (platinum complexed to divinyltetramethylsiloxane dissolved in polydimethyl-siloxane, platinum content=2 wt %) . . . 0.5 g The curable composition was mixed and degassed.

A cross-linker mixture was formed using the following components:

Methylhydrosiloxane-dimethylsiloxane copolymer having a viscosity of 45 cSt, hydride content of 1.7 mmol/g . . . 68.7 g Polydimethylsiloxane, hydride terminated having a viscosity of 15 cSt . . . 23.2 g Harwick Pigment 83SP01 (available from Harwick Chemical Company, Akron, Ohio) . . . 8.1 g A small capsule having dimensions of about ¼ inch diameter and 1 to 1.5 inch length was prepared using two sheets of Saran film (available from Dow Chemicals). The capsule was formed by heat sealing three sides of the sheets using an impulse sealer from American International Electric. About 0.9 g of the cross-linker/pigment mixture was placed in the capsule. Air was removed from the capsule and the fourth side was heat sealed.

The capsule and about 100 g of the curable composition were inserted into the bag through a fill port. The fill port was then sealed using the impulse sealer from American International Electric. The bag was trimmed to make the self-forming prosthetic device precursor.

The capsule inside the precursor was squeezed to burst the capsule. The contents of the capsule were then forced into the curable composition (i.e., similar to emptying a tube of toothpaste). The precursor was kneaded for about 5 to 10 minutes and then placed in a cradle. The precursor was allowed to cure for about 15 minutes. The self-forming prosthetic device conformed to the shape of the cradle.

EXAMPLE 6

Formation of a Self-Forming Prosthetic Device Having Hook Material Attached Thereto A self-forming prosthetic device was formed using the following procedure. A bag was formed by heat sealing two sheets of polyurethane film having a thickness of 2.5 mil. at a temperature of about 385° F. and a pressure of about 25 bar for about 2 seconds.

A curable material was formed by mixing the following components:

Polydimethylsiloxane having a viscosity of 100 cSt . . . 750.0 g

Vinyldimethylsiloxy terminated polydimethylsiloxane having a viscosity of 2,000 cSt . . . 200.0 g Vinyldimethylsiloxy terminated polydimethylsiloxane having a viscosity of 65,000 cSt . . . 50.0 g Platinum catalyst (platinum complexed to divinyltetramethylsiloxane dissolved in polydimethyl-siloxane, platinum content=2 wt %) . . . 0.5 g The curable composition was mixed and degassed.

A cross-linker mixture was formed using the following components:

Methylhydrosiloxane-dimethylsiloxane copolymer having a viscosity of 45 cSt, hydride content of 1.7 mmol/g . . . 68.7 g Polydimethylsiloxane, hydride terminated having a viscosity of 15 cSt . . . 23.2 g Harwick Pigment 8SP01 (available from Harwick Chemical Company) . . . 8.1 g A small capsule having dimensions of about ¼ inch diameter and 1 to 1.5 inch length was prepared using two sheets of Saran film (available from Dow Chemicals). The capsule was formed by heat sealing three sides of the sheets using an impulse sealer from American International Electric. About 1.0 g of the cross-linker/pigment mixture was placed in the capsule. Air was removed from the capsule and the fourth side was heat sealed.

The bag was positioned in a mold so that the fill port was accessible and curable composition placed in the bag would not leak from the bag. The capsule and about 100 g of the curable composition were inserted into the bag through the fill port. A piece of hook material (i.e., VELCRO™) was placed in the mold so that the hooks faced the mold surface and the back of the material touched the bag. The back of the hook material was coated with a heat seal polyurethane adhesive. The mold was heated at approximately 120° C. for about 30 minutes to thermally form the precursor bag into a desired shape, attach the hook material to the bag, and to heat seal the fill port.

After the mold cooled, the bag was removed. The bag was trimmed to make the self-forming prosthetic device precursor.

The capsule inside the precursor was squeezed to burst the capsule. The contents of the capsule were then forced into the curable composition (i.e., similar to emptying a tube of toothpaste). The precursor was kneaded for about 5 to 10 minutes and then placed in a cradle. The precursor was allowed to cure for about 15 minutes. The self-forming prosthetic device conformed to the shape of the cradle.

EXAMPLE 7

Formation of a Self-Forming Prosthetic Device Containing a Lightweight Filler Material A self-forming prosthetic device was formed using the following procedure. A bag was formed by heat sealing two sheets of polyurethane film having a thickness of 2.5 mil. at a temperature of about 385° F. and a pressure of about 25 bar for about 2 seconds.

A curable material was formed by mixing the following components:

Polydimethylsiloxane having a viscosity of 100 cSt . . . 74.4 g

Vinyldimethylsiloxy terminated polydimethylsiloxane having a viscosity of 2,000 cSt . . . 19.8 g Vinyldimethylsiloxy terminated polydimethylsiloxane having a viscosity of 65,000 cSt . . . 5.0 g Methylhydrosiloxane-dimethylsiloxane copolymer having a viscosity of 45 cSt, hydride content of 1.7 mmol/g . . . 0.6 g Polydimethylsiloxane, hydride terminated having a viscosity of 15 cSt . . . 0.2 g Filler material (polyacrylonitrile microspheres having an average particle size of 60–90 micrometers and a density of about 30 kg/m$^3$) . . . 4.0 g The curable composition was mixed and degassed.

A catalyst mixture was formed using the following components:

Platinum catalyst (platinum complexed to divinyltetramethylsiloxane dissolved in polydimethyl-siloxane, platinum content=2 wt %) . . . 10.0 g Polydimethylsiloxane, having a viscosity of 100 cSt . . . 74.0 g Harwick Pigment 83SP01 (available from Harwick Chemical Company) . . . 16.0 g A small capsule having dimensions of about ¼ inch diameter and 1 to 1.5 inch length was prepared using two sheets of Saran film (available from Dow Chemicals). The capsule was formed by heat sealing three sides of the sheets using an impulse sealer from American International Electric. About 0.5 g of the catalyst mixture was placed in the capsule. Air was removed from the capsule and the fourth side was heat sealed.

The capsule and about 48 g of the curable composition were inserted into the bag through a fill port. The fill port was sealed using an impulse sealer from American International Electric. Excess film of the bag was trimmed to make the self-forming prosthetic device precursor.

The capsule inside the precursor was squeezed to burst the capsule. The contents of the capsule were then forced into the curable composition (i.e., similar to emptying a tube of toothpaste). The precursor was kneaded for about 5 to 10 minutes and then placed in a cradle. The precursor was allowed to cure for about 15 minutes. The self-forming prosthetic device conformed to the shape of the cradle.

The resulting prosthetic device was lightweight compared to other prosthetic devices made without the filler material.

The above examples are only illustrative of various aspects of the present invention. It should be noted that many other variations of the examples are within the scope of the present invention. For example, the pigment material may be added to the curable material as opposed to the capsule material as shown in Example 5. Further, other attachments may be attached to the precursor bag using the same method as described in Example 6.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of making an article of manufacture comprising:

forming a prosthetic device precursor; the precursor including at least two separate compartments A and B, respectively; compartment A containing a curable material and compartment B containing at least one catalyst or at least one cross-linking agent, respectively;

positioning the precursor next to a patient's body; and curing the precursor to form the article of manufacture; wherein the article of manufacture substantially conforms to a contour of the patient's body.

2. The method of claim 1, further comprising a mixing step performed after the forming step, wherein said mixing step comprises mixing the curable material of compartment A with the at least one catalyst or the at least one cross-linking agent of compartment B.

3. The method of claim 1, wherein one of compartments A and B comprises a bag, and the other of compartments A and B comprises a capsule within the bag.

4. The method of claim 1, wherein the prosthetic device precursor comprises a multi-chamber bag, and wherein compartments A and B are separate chambers within the bag, separated from one another by an interior film.

5. The method of claim 3, wherein the bag comprises a polyurethane film material and the capsule comprises a polyethylene or a vinylidene chloride-containing copolymer film material.

6. The method of claim 4, wherein the bag comprises a first film material, and the interior film comprises a second film material, and wherein said first film material has a higher burst strength than said second film material.

7. The method of claim 3, wherein the bag further comprises a valve.

8. The method of claim 3, wherein the bag is treated using one or more of the following: thermoforming, laminating, embossing, texturing, and pigmenting.

9. The method of claim 1, further comprising positioning the precursor between the patient's body and an article of clothing.

10. The method of claim 9, wherein the article of clothing is a bra.

11. The method of claim 10, wherein the bra comprises attachment means for attaching the precursor to the bra.

12. A prosthetic device precursor comprising at least two separate compartments A and B, wherein compartment A contains a curable material and compartment B contains at least one of a catalyst and a cross-linking agent.

13. The prosthetic device precursor of claim 12, wherein one of compartments A and B comprises a bag, and the other of compartments A and B comprises a capsule within the bag.

14. The prosthetic device precursor of claim 12, wherein the prosthetic device precursor comprises a multi-chamber bag, and wherein compartments A and B are separate chambers within the bag, separated from one another by an interior film.

15. The prosthetic device precursor of claim 13, wherein the bag comprises a polyurethane film material and the capsule comprises a polyethylene or a vinylidene chloride-containing copolymer film material.

16. The prosthetic device precursor of claim 12, wherein the bag comprises a first film material, and the interior film comprises a second film material, and wherein said first film material has a higher burst strength than said second film material.

17. The prosthetic device precursor of claim 12, further comprising attachment means for attaching the prosthetic device precursor to an article of clothing.

18. The prosthetic device precursor of claim 12, in combination with an article of clothing comprising a bra.

19. The prosthetic device precursor of claim 12, further comprising a valve for at least one of compartments A and B.

20. The prosthetic device precursor of claim 14 or claim 15, wherein the bag is treated using one or more of the following: thermoforming, laminating, embossing, texturing, and pigmenting.

21. A prosthetic device formed by curing the prosthetic device precursor of claim 12.

22. A method of making a self-forming prosthetic device for wear by a user, the method comprising the steps of:

sizing a precursor specific to the needs of the user, the precursor comprising a first compartment having a curable material housed therein and a second compartment having at least one catalyst or at least one cross-linking agent, respectively, housed therein;

mixing the curable material with the at least one catalyst or the at least one cross-linking agent;

positioning the precursor on an inner surface of a cup of a bra;

placing the bra about the user while positioning the precursor with respect to the body of the user;

curing the mixed materials within the precursor to self-form the prosthetic device in situ to the body of the user.

23. The method of claim 22, the step of positioning the precursor on the inner surface of the cup further comprising positioning at least one first hook and loop fastener on an exterior surface of the precursor and positioning at least one corresponding second hook and loop fastener on the inner surface of the cup so that the prosthetic device is directly affixed to the inner surface of the cup.

24. The method of claim 23, further comprising forming the at least one second hook and loop fastener as at least a portion of the inner surface of the cup.

25. The method of claim 22, further comprising forming the bra cup such that it is comprised of the first inner surface, a middle layer adjacent the inner surface, and an outer layer adjacent the middle layer and facing outwardly of the bra cup.

26. The method of claim 22, further comprising sizing the precursor to form a partial prosthetic breast.

27. The method of claim 22, further comprising sizing the precursor to form a full prosthetic breast.

28. A system for self-forming a prosthetic device for wear by a user, comprising:

a precursor sized to the needs of the user, the precursor comprising a first compartment having a curable material housed therein and a second compartment having at least one catalyst or at least one cross-linking agent, respectively, housed therein;

a bra having at least one cup, and an inner surface defined by said at least one cup;

means for affixing the precursor directly to the inner surface of the bra cup;

wherein the curable material of the first compartment is mixed with the at least one catalyst or the at least one cross-linking agent of the second compartment within the precursor, the precursor is affixed to the inner surface of the cup, the bra is placed about the chest of the user to position the precursor with respect to the body of the user, and the mixed materials within the precursor are cured in situ to self-form the prosthetic device to the body of the user.

29. The system of claim 28, said means for affixing the precursor directly to the inner surface of the bra cup comprising at least one first hook and loop fastener positioned on an exterior surface of the precursor, and at least one corresponding second hook and loop fastener positioned on the inner surface of the cup.

30. The system of claim 29, the inner surface of the bra cup comprising the at least one first hook and loop fastener.

31. The system of claim 28, the bra cup further comprising a foam layer adjacent the inner surface, and an outer fabric layer adjacent the second layer and facing outwardly of the bra cup.

32. The method of claim 28, wherein the precursor is sized and shaped to form a partial prosthetic breast.

33. The method of claim 28, wherein the precursor is sized and shaped to form a full prosthetic breast.

* * * * *